United States Patent [19]
Krenzer et al.

[11] 3,948,967
[45] *Apr. 6, 1976

[54] ARYL UREA CARBONATES

[75] Inventors: John Krenzer, Oak Park; Sidney B. Richter, Chicago, both of Ill.

[73] Assignee: Velsicol Chemical Corporation, Chicago, Ill.

[ * ] Notice: The portion of the term of this patent subsequent to Jan. 25, 1989, has been disclaimed.

[22] Filed: Aug. 26, 1974

[21] Appl. No.: 500,218

Related U.S. Application Data

[63] Continuation of Ser. No. 695,338, Jan. 3, 1968, Pat. No. 3,864,377.

[52] U.S. Cl. .................. 260/463; 71/98; 71/106; 424/301
[51] Int. Cl.² ............................ C07C 69/96
[58] Field of Search .......................... 260/463

[56] References Cited
UNITED STATES PATENTS

| | | | |
|---|---|---|---|
| 3,393,224 | 7/1968 | Brookes et al. | 260/463 X |
| 3,419,620 | 12/1968 | Becher et al. | 260/463 X |
| 3,637,795 | 1/1972 | Krenzer et al. | 260/463 |
| 3,864,377 | 2/1975 | Krenzer et al. | 260/463 |

*Primary Examiner*—Joseph P. Brust
*Attorney, Agent, or Firm*—Robert J. Schwarz; Dietmar H. Olesch

[57] ABSTRACT

New compounds of the formula

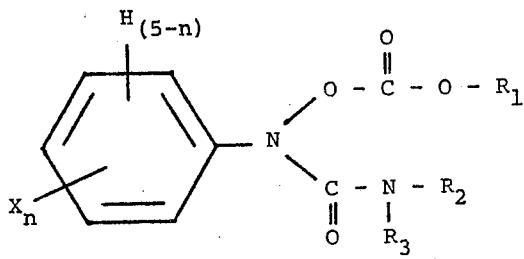

wherein each X is independently selected from the group consisting of halogen, alkyl, alkenyl, haloalkyl, nitro, alkoxy, alkylthio, alkylsulfoxide, alkylsulfone and dialkylamino; $n$ is an integer from 0 to 4; $R_1$ is selected from the group consisting of alkyl, alkenyl, haloalkyl, and

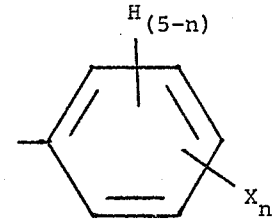

wherein X and $n$ are as heretofore described; and $R_2$ and $R_3$ are each independently selected from the group consisting of hydrogen, alkyl, alkenyl and haloalkyl. A herbicidal and fungicidal composition comprising an inert carrier and as an essential active ingredient, in a quantity toxic to weeds or fungi, a compound of the above description. A method for the control of weeds and fungi which comprises applying to said weeds or fungi a herbicidal or fungicidal composition comprising an inert carrier and, as an essential active ingredient, in a quantity toxic to weeds or fungi, a compound heretofore described.

3 Claims, No Drawings

ARYL UREA CARBONATES

This application is a continuation of copending application Ser. No. 695,338, filed Jan. 3, 1968, now issued into U.S. Pat. No. 3,864,377, on Feb. 4, 1975.

This invention relates to new compositions of matter; in particular this invention relates to new compounds of the formula

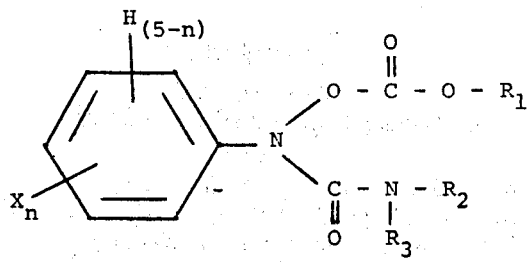

wherein each X is independently selected from the group consisting of halogen, alkyl, alkenyl, haloalkyl, nitro, alkoxy, alkylthio, alkylsulfoxide, alkylsulfone and dialkylamino; n is an integer from 0 to 4; $R_1$ is selected from the group consisting of alkyl, alkenyl, haloalkyl, and

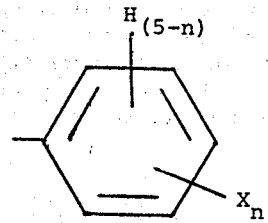

wherein X and n are as heretofore described; and $R_2$ and $R_3$ are each independently selected from the group consisting of hydrogen, alkyl, alkenyl and haloalkyl.

In a preferred embodiment of this invention each X is independently selected from the group consisting of chlorine, bromine, lower alkyl, lower alkenyl, lower chloroalkyl, lower bromoalkyl, nitro, lower alkoxy, lower alkylthio, lower alkylsulfoxide, lower alkylsulfone and di (lower alkyl)amino; n is an integer from 0 to 3; $R_1$ is selected from the group consisting of lower alkyl, lower alkenyl, lower haloalkyl and

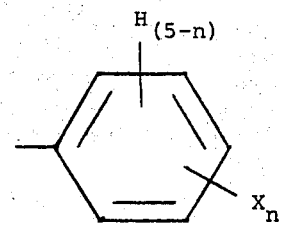

wherein X and n are as described; and $R_2$ and $R_3$ are each independently selected from the group consisting of hydrogen, lower alkyl, lower alkenyl and lower haloalkyl.

The compounds of this invention are unexpectedly useful as pesticides, particularly as herbicides and fungicides.

The new compounds of the present invention can be readily prepared by reacting a hydroxyurea of the formula

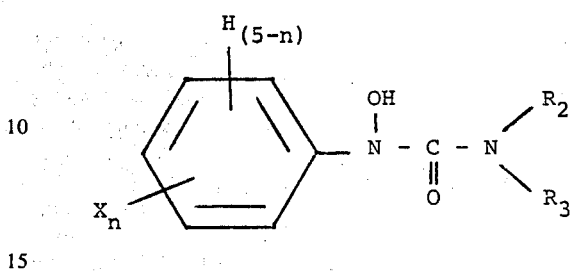

wherein X, n, $R_2$ and $R_3$ are as heretofore described, with a chloroformate of the formula

wherein $R_1$ is as heretofore described. This reaction can be readily carried out by adding the described chloroformate to a solution or slurry of the described hydroxyurea in the presence of a base, such as a tertiary amine or alkali metal hydroxide, at a temperature of from about 0° to about 50°C. The desired product can then be recovered by methods well known to the art, such as distillation, if the product remains in solution, filtration, if the product forms as a precipitate, and the like. The product can then be used as such or can be further purified by washing, recrystallizing and the like.

Exemplary suitable hydroxy ureas for the purpose of this invention are 1-(3,4-dibromophenyl)-1-hydroxy-3-methylurea, 1-(3,4-dichlorophenyl)-1-hydroxy-3-ethylurea, 1-(2-methyl-3-chlorophenyl)-1-hydroxy-3-methylurea, 1-(3-nitro-4-methylphenyl)-1-hydroxy-3-isopropylurea, 1-(3,4-dichlorophenyl)-1-hydroxy-3,3-dimethylurea, 1-(2-methoxy-4-chlorophenyl)-1-hydroxy-3-methylurea, 1-(4-trichloromethylphenyl)-1-hydroxy-3-methylurea, 1-(3-dimethylamino-4-chlorophenyl)-1-hydroxy-3-methylurea, 1-(4-allylphenyl)-1-hydroxy-3,3-diethylurea, 1-(3,4-dichlorophenyl)-1-hydroxyurea, 1-(3-methylthiophenyl)-1-hydroxy-3-ethylurea, 1-(4-ethysulfinylphenyl)-1-hydroxy-3-methylurea and the like.

Exemplary suitable chloroformates for the purpose of this invention are methyl chloroformate, ethyl chloroformate, n-propyl chloroformate, isopropyl chloroformate, n-butyl chloroformate, sec-butyl chloroformate, t-butyl chloroformate, allyl chloroformate, chloromethyl chloroformate, dibromomethyl chloroformate, trifluoromethyl chloroformate, β-chloroethyl chloroformate, phenyl chloroformate, 4-chlorophenyl chloroformate, 2,4-dibromophenyl chloroformate, 3,4-dichlorophenyl chloroformate, 3-chloro-4-methylphenyl chloroformate, 4-methoxyphenyl chloroformate, 4-nitrophenyl chloroformate, 2-dimethylaminophenyl chloroformate, 4-trichloromethylphenyl chloroformate and the like.

The manner in which the compounds of the present invention can be prepared readily is illustrated in the following examples.

EXAMPLE 1

Preparation of
1-(3,4-Dichlorophenyl)-1-methoxycarbonyloxy-3-methylurea

A solution of 1-(3,4-dichlorophenyl)-1-hydroxy-3-methylurea (15 grams; 0.06 mol) in isopropyl alcohol (50 ml), and pyridine (8 ml) were charged into a glass reaction flask equipped with a mechanical stirrer. Methyl chloroformate (7 ml; 0.09 mol) was then slowly added, with stirring, at a temperature of 10° to 15°C. After the addition was completed stirring was continued for an additional period of one-half hour resulting in the formation of a precipitate. After this time the reaction mixture was poured onto ice and the precipitate recovered by filtration. The precipitate was recrystallized first from a benzene-hexane mixture and then from a methyl alcohol-water mixture to yield 1-(3,4-dichlorophenyl)-1-methoxycarbonyloxy-3-methylurea having a melting point of 110°C with decomposition and having the following elemental analysis as calculated for $C_{10}H_{10}Cl_2N_2O_4$:

|  | C | H | Cl |
|---|---|---|---|
| Calculated %: | 40.96 | 3.44 | 24.19 |
| Found %: | 40.99 | 3.50 | 23.97 |

EXAMPLE 2

Preparation of
1-(3,4-Dichlorophenyl)-1-ethoxycarbonyloxy-3-methylurea

A solution of 1-(3,4-dichlorophenyl)-1-hydroxy-3-methylurea (15 grams; 0.06 mol) is isopropyl alcohol (50 ml), and pyridine (7 ml) were charged into a glass reaction vessel equipped with a mechanical stirrer. Ethyl chloroformate (7 ml; 0.09 mol) was then slowly added, with stirring, at a temperature of 10° to 15°C. After the addition was completed stirring was continued for an additional period of about one-half hour resulting in the formation of a precipitate. After this time, the reaction mixture was poured onto ice and the precipitate recovered by filtration. The precipitate was recrystallized from a benzene-hexane mixture to yield 1-(3,4-dichlorophenyl)-1-ethoxycarbonyloxy-3-methylurea having a melting point of 97°–98°C and having the following elemental analysis as calculated for $C_{11}H_{12}Cl_2N_2O_4$:

|  | C | H | Cl |
|---|---|---|---|
| Calculated %: | 43.07 | 3.94 | 23.08 |
| Found %: | 43.04 | 4.13 | 23.06 |

EXAMPLE 3

Preparation of
1-(2,5-Dichlorophenyl)-1-ethoxycarbonyloxy-3-methylurea

A solution of 1-(2,5-dichlorophenyl)-1-hydroxy-3-methylurea (22 grams; 0.09 mol) in 2 N sodium hydroxide (50 ml) was charged into a glass reaction flask equipped with a mechanical stirrer. Ethyl chloroformate (9.6 ml; 0.1 mol) was added to the flask at a temperature of about 10° to 15°C. After the addition the reaction mixture was stirred for a period of about one-half hour, during which time a precipitate was formed. The precipitate was recovered by filtration and was recrystallized from isopropyl alcohol to yield 1-(2,5-dichlorophenyl)-1-ethoxycarbonyloxy-3-methylurea having a melting point of 130° to 132°C and having the following elemental analysis as calculated for $C_{11}H_{12}Cl_2N_2O_4$:

|  | C | H | Cl |
|---|---|---|---|
| Calculated %: | 43.07 | 3.94 | 23.08 |
| Found %: | 43.23 | 4.14 | 23.19 |

EXAMPLE 4

Preparation of
1-(4-Chlorophenyl)-1-methoxycarbonyloxy-3-methylurea

A solution of 1-(4-chlorophenyl)-1-hydroxy-3-methylurea (10 grams; 0.05 mol) in isopropyl alcohol (40 ml), and pyridine (6 ml) were charged into a glass reaction flask equipped with a mechanical stirrer. Methyl chloroformate (5 ml; 0.06 mol) was added to the flask with stirring, at a temperature of about 10° to 15°C. After the addition was completed the reaction mixture was stirred for an additional one-half hour resulting in the formation of a precipitate. After this time, the reaction mixture was poured onto ice and the precipitate was recovered by filtration and dried. The dried precipitate was then recrystallized from a methyl alcohol-water mixture to yield 1-(4-chlorophenyl)-1-methoxycarbonyloxy-3-methylurea having a melting point of 145° to 146°C and having the following elemental analysis as calculated for $C_{10}H_{11}ClN_2O_4$:

|  | C | H | Cl |
|---|---|---|---|
| Calculated %: | 46.43 | 4.29 | 13.71 |
| Found %: | 46.62 | 4.49 | 13.64 |

EXAMPLE 5

Preparation of
1-(3,4-Dichlorophenyl)-1-phenoxycarbonyloxy-3,3-dimethylurea

A solution of 1-(3,4-dichlorophenyl)-1-hydroxy-3,3-dimethylurea (12.5 grams; 0.05 mol) in isopropyl alcohol (40 ml), and pyridine (6 ml) are charged into a glass reaction flask equipped with a mechanical stirrer. Phenyl chloroformate (7.8 grams; 0.05 mol) is added to the flask, with stirring, at a temperature of about 10° to 15°C. After the addition is completed, the reaction mixture is stirred for an additional period of about one-half hour resulting in the formation of a precipitate. After this time, the reaction mixture is poured onto ice and the precipitate is recovered by filtration and is dried. The dried precipitate is recrystallized to yield 1-(3,4-dichlorophenyl)-1-phenoxycarbonyloxy-3,3-dimethylurea.

EXAMPLE 6

Preparation of
1-(3,4-Dichlorophenyl)-1-phenoxycarbonyloxy-3-methylurea

A solution of 1-(3,4-dichlorophenyl)-1-hydroxy-3-methylurea (6 grams; 0.025 mol) in diethyl ether (200 ml), and triethylamine (4 ml) were charged into a glass reaction flask equipped with a mechanical stirrer. Phenyl chloroformate (4.2 grams; 0.027 mol) was added thereto. The reaction mixture was stirred, at room temperature, for a period of about one-half hour resulting in the formation of a precipitate. The precipitate was recovered by filtration, was washed with water, dried, and was recrystallized from a methylene chloride-pentane mixture to yield 1-(3,4-dichlorophenyl)-1-phenoxycarbonyloxy-3-methylurea melting at 93°C with decomposition and having the following elemental analysis as calculated for $C_{15}H_{12}Cl_2N_2O_4$:

|  | C | H | N |
|---|---|---|---|
| Calculated %: | 50.73 | 3.38 | 7.88 |
| Found %: | 50.22 | 3.41 | 7.92 |

Other compounds within the scope of this invention can be prepared by the procedures described in the foregoing examples. Presented in the following examples are the essential ingredients required to prepare the indicated named compounds according to the procedures heretofore described.

EXAMPLE 7

1-(3,4-Dibromophenyl)-1-hydroxy-3-methylurea + ethyl chloroformate = 1-(3,4-dibromophenyl)-1-ethoxycarbonyloxy-3-methylurea.

EXAMPLE 8

1-(3-Methyl-4-chlorophenyl)-1-hydroxy-3-methylurea + methyl chloroformate = 1-(3-methyl-4-chlorophenyl)-1-methoxycarbonyloxy-3-methylurea.

EXAMPLE 9

1-(3,4-Dichlorophenyl)-1-hydroxyurea + isopropyl chloroformate = 1-(3,4-dichlorophenyl)-1-isopropyloxycarbonyloxyurea.

EXAMPLE 10

1-(4-Methoxyphenyl)-1-hydroxy-3,3-dimethylurea + chloromethyl chloroformate = 1-(4-methoxyphenyl)-1-chloromethoxycarbonyloxy-3,3-dimethylurea.

EXAMPLE 11

1-(2,4-Dinitrophenyl)-1-hydroxy-3-isopropylurea + methyl chloroformate = 1-(2,4-dinitrophenyl)-1-methoxycarbonyloxy-3-isopropylurea.

EXAMPLE 12

1-(3,4-Dichlorophenyl)-1-hydroxy-3-methylurea + 3,4-dichlorophenyl chloroformate = 1-(3,4-dichlorophenyl)-1-(3,4-dichlorophenoxycarbonyloxy)-3-methylurea.

EXAMPLE 13

1-(3,4-Dichlorophenyl)-1-hydroxy-3-methylurea + 4-methyl-4-chlorophenyl chloroformate = 1-(3,4-dichlorophenyl)-1-(3-methyl-4-chlorophenoxycarbonyloxy)-3-methylurea.

EXAMPLE 14

1-(3-Methylthiophenyl)-1-hydroxy-3-methylurea + methyl chloroformate = 1-(3-methylthiophenyl)-1-methoxycarbonyloxy-3-methylurea.

EXAMPLE 15

1-(4-Methylsulfonylphenyl)-1-hydroxy-3-ethylurea + ethyl chloroformate = 1-(4-methylsulfonylphenyl)-1-ethoxycarbonyloxy-3-ethylurea.

EXAMPLE 16

1-(4-Ethylsulfinylphenyl)-1-hydroxy-3-methylurea + phenyl chloroformate = 1-(4-ethylsulfinylphenyl)-1-phenoxycarbonyloxy-3-methylurea.

EXAMPLE 17

1-(4-Trifluoromethylphenyl)-1-hydroxy-3-methylurea + methyl chloroformate = 1-(4-trifluoromethylphenyl)-1-methoxycarbonyloxy-3-methylurea.

additional compounds within the scope of this invention which can be prepared in a manner similar to that detailed in the foregoing examples but which are not to be construed as limiting this invention are 1-(2,5-dimethylphenyl)-1-methoxycarbonyloxy-3-methylurea, 1-(3,4-dichlorophenyl)-1-(2-methyl-5-chlorophenoxycarbonyloxy)-3-methylurea, 1-(3,4-dichlorophenyl)-1-(2,6-dimethoxy-4-chlorophenoxycarbonyloxy)-3,3-dimethylurea, 1-(3,4,5-trichlorophenyl)-1-methoxycarbonyloxy-3-methylurea, 1-(3,5-dimethylphenyl)-1-methoxycarbonyloxy-3-trichloromethylurea and the like.

For practical use as pesticides, the compounds of this invention are generally incorporated into pesticidal compositions which comprise an inert carrier and a pesticidally toxic amount of such a compound. Such pesticidal compositions, which can also be called formulations, enable the active compound to be applied conveniently to the site of the pest infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of pesticides can be dispersed under superatmospheric pressure as aerosols. However, preferred liquid pesticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the pest infestation. The emulsifiers most commonly used in these concentrates are nonionic or mixtures of nonionic with anionic surface-active agents. With the use of some emulsifier systems an inverted emulsion (water-in-oil) can be prepared for direct application to pest infestations.

A typical pesticidal composition according to this invention is illustrated by the following example, in which the quantities are in parts by weight.

EXAMPLE 18

Preparation of a Dust

| Product of Example 1 | 10 |
|---|---|
| Powdered talc | 90 |

The above ingredients are mixed in a mechanical grinder-blender and are ground until a homogeneous, free-flowing dust of the desired particle size is obtained. This dust is suitable for direct application to the site of the pest infestation. For the purpose of this invention the term pesticide is used to designate herbicide or fungicide.

When used as herbicides, the compounds of this invention can be applied in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers; spreaders; deactivators; adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5 to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)-piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, o-S-dimethyl tetrachlorothioterephthalate, methyl 2,3,5,6-tetrachloro-N-methoxy-N-methylterephthalamate, 2-[(4-chloro-o-tolyl)-oxy]-N-methoxyacetamide, DSMA, MSMA, potassium azide, acrolein, benefin, bensulide, AMS, bromacil, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose-grass, chickweed, wild oats, velvetleaf, purslane, barnyardgrass, smartweed, knotweed, cocklebur, wild buckwheat, kochia, medic, corn cockle, ragweed, sowthistle, coffee-weed, croton, cuphea, dodder, fumitory, groundsel, hemp nettle, knawel, spurge, spurry, emex, jungle rice, pondweed, dog fennel, carpetweed, morningglory, bedstraw, ducksalad and naiad; biennials such as wild carrot, matricaria, wild barley, campion, chamomile, burdock, mullein, roundleaved mallow, bull thistle, hounds-tongue, moth mullein and purple star thistle; or perennials such as white Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of California barnyardgrass, crabgrass, dock, downybrome, foxtail, Johnson grass, mustard weed, pigweed and velvet leaf. In these experiments small plastic greenhouse pots filled with dry soil were seeded with California barnyardgrass, crabgrass, dock, downybrome, foxtail, Johnson grass, mustard weed, pigweed and velvetleaf. Twenty-four hours or less after seeding the pots were sprayed with water until the soil was wet and the test compounds formulated as aqueous emulsions of acetone solutions containing emulsifiers were sprayed at the rate of 8 lb. per acre on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death.

The herbicidal activity of the compounds of this invention was also demonstrated by experiments carried out for the post-emergence control of California barnyardgrass, crabgrass, dock, downybrome, foxtail, Johnson grass, mustard weed, pigweed and velvetleaf. In these experiments the compounds to be tested were formulated as aqueous emulsions and sprayed at the rate of 8 lb. per acre on the foliage of California barnyardgrass, crabgrass, dock, downybrome, foxtail, Johnson grass, mustard weed, pigweed and velvetleaf that had attained a prescribed size. After spraying the plants were placed in a greenhouse and watered daily or more frequently. Water was not applied to the foliage of the treated plants. The severity of the injury was determined 10 to 15 days after treatment and was rated on the scale of from 0 to 10 heretofore described. The effectiveness of these compounds as pre- and post-emergence herbicides is demonstrated by the following data:

TABLE I

| Test Compound | Weed Species | Injury Rating | |
|---|---|---|---|
| | | Pre-Emergence | Post-Emergence |
| Product of Example 1 | California barnyard-grass | 9.5 | 10 |
| " | Crabgrass | 10 | 10 |
| " | Dock | 9.5 | 8 |
| " | Downybrome | 9 | 10 |
| " | Foxtail | 10 | 10 |
| " | Johnson grass | 9 | 8 |
| " | Mustard | 10 | 10 |
| " | Pigweed | 10 | 10 |
| " | Velvetleaf | 10 | 10 |
| Product of Example 2 | California barnyard-grass | 10 | 10 |
| " | Crabgrass | 10 | 10 |
| " | Dock | 9 | 9 |
| " | Downybrome | 9 | 10 |
| " | Foxtail | 10 | 10 |
| " | Johnson grass | 8 | 8 |
| " | Mustard | 10 | 10 |
| " | Pigweed | 10 | 10 |
| " | Velvetleaf | 10 | 10 |

The new compounds of this invention are fungicidal in their ability to kill, inhibit, or inactivate a fungus so that it does not grow. Practically, these compounds can be used to prevent fungi and molds from harming cloth, wood, plants, seeds, fruit, animals, or whatever else they attack. The fungicidal compound should preferably be applied before the infection has occurred and certainly before it has progressed very far.

When used as fungicides the compounds of this invention can be applied in any manner recognized by the art. The concentration of the new compounds of this invention in the fungicidal compositions will vary greatly with the type of formulation and the purpose for which it is designed, but generally the fungicidal compositions will comprise from about 0.05 to about 95 percent by weight of the active compounds of this invention. In a preferred embodiment of this invention, the fungicidal compositions will comprise from about 5 to about 75 percent by weight of the active compound. The compositions can also comprise such additional substances as other pesticides, spreaders, adhesives, stickers, fertilizers, activators, synergists, and the like.

The compounds of the present invention are also useful when combined with other fungicides in the fungicidal compositions heretofore described. The other fungicides can comprise from about 5 to about 95% of the active ingredients in the fungicidal compositions. Use of combinations of these other fungicides with the compounds of the present invention provides fungicidal compositions which are more effective in controlling fungi and often provide results unattainable with separate compositions of the individual fungicides. The other fungicides, with which the compounds of this invention can be used in the fungicidal compositions to control fungi, can include fungicides such as 2-aminobutane, bordeaux mixture, ammonium dimethyl dithiocarbamate, benzoyl trimethyl ammonium bromide, cadmium sulfate, captan, chloranil, copper sulfate, cycloheximide, dichlone, 2,4-dichloro-6-(2-chloroanilino)-s-triazine, DDT, dichloran, p-dimethylaminobenzenediazo sodium sulfonate, zinocap, diphenylmercuri 8-hydroxyquinolinate, dodine, ethylmercuric chloride, ferban, folpet, ferbam, maneb, metham, mezineb, nabam, pentachloronitrobenzene, PMA, phenylmercuric urea, streptomicin, thiram, zineb, ziram, difolatan, PCNB, and the like.

Such fungicides can also be used in the methods and compositions of this invention in the form of their esters, amides, and other derivatives whenever applicable to the particular parent compounds.

When the compounds of this invention are used as agricultural fungicides, they can be applied to plant foliage, to seeds, to the soil, or to such parts of plants as the fruits themselves. Plants are susceptible to a great many diseases which cause widespread damage; and among some of the more important which can be mentioned are late blight on tomato, powdery mildew on cucumber (*Erisiphe cichoracearum*), cereal leaf rust on wheat (*Puccinia rubigo-vera*), and such common soil fungi as fusarium wilt (*Fusarium oxysporum*), the seed rot fungus (*Phythium debaranum*), and the sheath and culm blight (*Rhizoctonia solani*). The new compounds of this invention can also be employed as industrial fungicides to control a variety of fungi which attack such materials as adhesives, cork, paints, lacquers, leather, wood, plastics, and textiles such as cotton and wool.

The quantity of active compound of this invention to be used for good disease control will depend on a variety of factors, such as the particular disease involved, the intensity of the infestation, formulation, weather, type of crop and the like. Thus, while the application of only one or two ounces of active compound per acre of a crop may be sufficient to control a light infestation of certain fungi, a pound or more of active compound per acre may be required to control a heavy infestation of a hardy species of fungus.

The fungicidal utility of the compounds of this invention was illustrated by experiments carried out for the control of leaf rust on wheat, *Puccinia rubigo-vera*. In these experiments wheat plants were grown in soil until they were about 2–2½ inches tall. The soil in which the plants were growing was then watered with about 25 cc. of a solution of the chemical in water. The plants were then placed in the greenhouse for about five days and inoculated with leaf rust spores by dusting the spores from diseased plants. After 7 to 10 days the growth of the fungus on the plants was measured and rated in comparison with plants inoculated but otherwise untreated. The results of these experiments are presented below:

TABLE II

| Test Compound | Concn. Actual Compound, ppm | % Control |
| --- | --- | --- |
| Product of Example 1 | 200 | 100 |
| Product of Example 2 | 200 | 100 |
| Product of Example 3 | 1000 | 95 |

We claim:
1. A compound of the formula

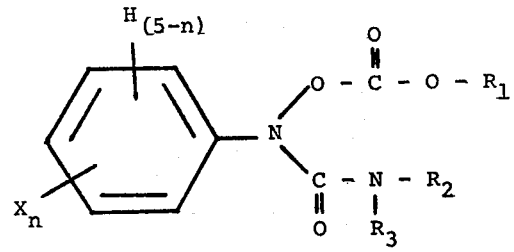

wherein each X is independently selected from the group consisting of chlorine, bromine, lower alkyl, lower alkenyl, lower chloroalkyl, lower bromoalkyl, nitro, lower alkoxy, lower alkylthio and di(lower alkyl)amino; n is an integer from 0 to 3; $R_1$ is wherein each X is independently selected from the group consisting of chlorine, bromine, lower alkyl, lower chloroalkyl, lower bromoalkyl, nitro, lower alkoxy and di(lower alkyl)amino; n is an integer from 0 to 3; and $R_2$ and $R_3$ are independently selected from the group consisting of hydrogen, lower alkyl and lower haloalkyl.

2. The compound of claim 1, 1-(3,4-dichlorophenyl)-1-phenoxycarbonyloxy-3,3-dimethylurea.

3. The compound of claim 1, 1-(3,4-dichlorophenyl)-1-(3-methyl-4-chlorophenoxycarbonyloxy)-3-methylurea.

* * * * *